(12) United States Patent
Döring et al.

(10) Patent No.: US 6,372,912 B1
(45) Date of Patent: Apr. 16, 2002

(54) PROCESS FOR RING CLEAVAGE OF THIAZOLIDINE DERIVATIVES

(75) Inventors: Wolfgang Döring, München; Günther Karl Staudinger, deceased, late of Münich, both of (DE), by Gerda Irmtraud Staudinger and Andreas Josef Staudinger, heirs

(73) Assignee: Consortium fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/543,634

(22) Filed: Apr. 5, 2000

(30) Foreign Application Priority Data

Apr. 27, 1999 (DE) .......................................... 199 19 336

(51) Int. Cl.⁷ ...................... C07D 277/04; C07C 319/06
(52) U.S. Cl. ...................... 548/147; 548/200; 548/201; 560/147; 562/557; 562/558; 564/198
(58) Field of Search ................................ 548/147, 200, 548/201; 560/147; 562/557, 558; 564/198

(56) References Cited

U.S. PATENT DOCUMENTS

| | | | |
|---|---|---|---|
| 3,300,508 A | 1/1967 | Shimizu et al. | 266/306.7 |
| 3,888,923 A | 6/1975 | Asinger et al. | 260/534 |
| 4,731,477 A * | 3/1988 | Koban et al. | 562/558 |

FOREIGN PATENT DOCUMENTS

| | | |
|---|---|---|
| DE | 1 795 297 | 2/1972 |
| DE | 2 142 336 | 3/1973 |
| DE | 3607 167 A1 | 9/1987 |
| EP | 0 213 785 A1 | 8/1986 |
| EP | 0 235 376 A1 | 12/1986 |

OTHER PUBLICATIONS

Grant, R.L. and Hackh, I.W.D., "Grant & Hackh's chemical dictionary", 1987, McGraw–Hill, New York, p. 211.*
Nagai, U and Pavone, V., Heterocycles, 28, 1989, 589–592.*
Copploa, Gary M, Synthesis, 1984, 1021–1023.*
Fieser, Louis F and Feiser, Mary "Reagents for Organic Synthesis", 1968, John Wiley, New York, 511–512.*
Ullmann's Encyclopedia Of Industrial Chemistry, vol. A14, p. 451.
English Derwent Abstract [AN 1987–251130[36]] Corresponding To EP 0 235 376.
English Derwent Abstract [AN 1973–10884U[08]] Corresponding To DE 2 142 336.
English Derwent Abstract [AN 1970–17346R[11]] Corresponding To DE 1795 297.
English Derwent Abstract [AN 1987–251130[36]] Corresponding To DE 36 07 167.

* cited by examiner

Primary Examiner—Mukund J. Shah
Assistant Examiner—Thomas C McKenzie
(74) Attorney, Agent, or Firm—Brooks & Kushman P.C.

(57) ABSTRACT

Process for the hydrolytic ring cleavage of thiazolidine derivatives to give 2-aminomercaptan derivatives and carbonyl compounds, which comprises bringing an aqueous solution of the thiazolidine derivative into contact with an acidic cation exchanger in the $H^+$ form, giving a solution $L_1$ which contains the carbonyl compound and eluting the cation exchanger with a suitable eluent, giving a solution $L_2$ which contains the 2-aminomercaptan derivative.

10 Claims, No Drawings

PROCESS FOR RING CLEAVAGE OF THIAZOLIDINE DERIVATIVES

TECHNICAL FIELD

The invention relates to a process for the hydrolytic ring cleavage of thiazolidine derivatives.

BACKGROUND ART

The acid- or base-catalyzed hydrolysis of thiazolidine derivatives to give the corresponding (substituted) 2-aminomercaptan derivatives and (substituted) aldehydes or ketones is known.

Depending on the degree of substitution at the 2 position, thiazolidine derivatives have highly differing hydrolytic stabilities. Whereas 2,2-disubstituted thiazolidine derivatives derived from the corresponding ketones are, in most cases, quite susceptible to hydrolysis, 2-monosubstituted thiazolidine derivatives, derived from the corresponding aldehydes, are relatively stable to hydrolytic ring cleavage. Electron-withdrawing groups in the α position in 2,2-disubstituted thiazolidines also render these derivatives relatively stable to hydrolysis.

In order to cleave thiazolidine derivatives which are not very susceptible to hydrolysis, in general, one of the hydrolysis products is removed from the equilibrium mixture. In the case of thiazolidine derivatives which release a volatile carbonyl compound during hydrolysis, this compound can be removed from the equilibrium, for example, by distillation. In DE-A 1795297, isobutyraldehyde is removed from 2-isopropyl-5,5-dimethylthiazolidine-4-carboxylic acid (hydrochloride) by steam distillation, to obtain DL-penicillamine (hydrochloride). In this process, approximately 25 l of water have to be evaporated per mole of thiazolidine derivative. The long reaction time at high temperatures under acidic or alkaline conditions is a considerable disadvantage. In the case of sensitive compounds, this may lead to decomposition or, for example in the case of optically active compounds, to racemization.

A further process for cleaving thiazolidine derivatives which are not very susceptible to hydrolysis is reaction of the carbonyl compound that is liberated during hydrolysis with a "carbonyl reagent" such as hydroxylamine, which reacts with the carbonyl groups with high efficiency under the reaction conditions. DE-A 2142336 describes the ring cleavage of 2-isopropyl-5,5-dimethylthiazolidine compounds by reaction with a carbonyl reagent. Suitable carbonyl reagents are, for example, hydrazine, phenylhydrazine, 2,4-dinitrophenylhydrazine, semicarbazide, thiosemicarbazide and, in particular, hydroxylamine. Disadvantageous here is the fact that it is often difficult or even impossible to regenerate the carbonyl compound afterwards.

Alternatively, the acidic hydrolysis can be carried out at temperatures above 100° C., i.e. in an autoclave under pressure. This is described, for example, in DE-A 3607167. However, relatively long reaction times under drastic conditions are harmful in the case of temperature-sensitive compounds or, for example in the case of optically active compounds, lead to racemization.

A further possibility of cleaving thiazolidine derivatives which are not very susceptible to hydrolysis consists in the oxidative removal of the liberated aminomercaptan derivative from the equilibrium by conversion into the corresponding disulfide. However, if the mercaptan is the desired target compound, this has to be recovered subsequently in a further reductive reaction step. EP 213785 A1 describes the reaction of (4R)-thiazolidine-4-carboxylic acid with hydrogen peroxide to give L-cystine, which is subsequently reduced electrolytically to L-cysteine.

DISCLOSURE OF INVENTION

It is the object of the present invention to provide a process for the hydrolytic cleavage of thiazolidine derivatives, in particular of thiazolidine-4-carboxylic acids and thiazolidine-4-carboxylic acid derivatives, which avoids the disadvantages of the prior art and yields, in particular, both the 2-aminomercaptan derivative and the carbonyl compound in high yield and purity. Furthermore, the percent invention provides a process which is simple, and cost-effective to carry out on an industrial scale. The process is amenable not only to difficulty cleavable thiazolidines, but can be used to advantage even for thiazolidines which are considered readily susceptible to hydrolysis.

BEST MODE FOR CARRYING OUT THE INVENTION

The invention provides a process for the hydrolytic ring cleavage of thiazolidine derivatives to give 2-aminomercaptan derivatives and carbonyl compounds, which comprises a) contacting an aqueous solution of the thiazolidine derivative with an acidic cation exchanger in the H$^+$ form, giving a solution L$_1$ which contains the carbonyl compound and b) eluting the cation exchanger with a suitable eluent, giving a solution L$_2$ which contains the 2-aminomercaptan derivative.

The thiazolidine derivatives used are preferably compounds of the formula 1:

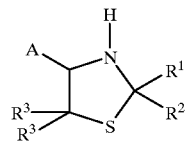

where

A is CN, COOR$^4$ or CONR$^5$R$^6$;

R$^4$ is selected from the group consisting of H, and linear or branched C$_1$- to C$_{12}$-alkyl radicals;

R$^5$ and R$^6$ are identical or different and are H or a linear or branched C$_1$- to C$_{12}$-alkyl radical;

R$^1$ and R$^2$ are identical or different and are selected from the group consisting of H, a linear or branched C$_1$- to C$_{12}$-alkyl, a C$_1$- to C$_6$-alkyl mono- or polysubstituted by alkoxy or hydroxyl, (CH$_2$)$_n$COOR$^4$, where n is an integer from 0 to 12 and R$^4$ is as defined above, phenyl mono- or poly-(C$_1$, to C$_6$ alkyl) substituted 1-naphthyl, 2-naphthyl, 9-phenanthrenyl, and 5- or 6-membered heteroaryl having 1 to 3 identical or different heteroatoms from the group consisting of O, N and S, and where the radicals R$^1$ and R$^2$ together comprise a C$_2$- to C$_9$-cycloalkyl radical and R$^3$ is H or methyl. Particular preference is given to using thiazolidine derivatives which have a solubility in water of at least 1 g/l at 25° C. and atmospheric pressure.

Most preferably, the process is employed for cleaving thiazolidine derivatives which, after the reaction, give a compound selected from the group consisting of cysteine, cysteine methyl ester, cysteine ethyl ester, penicillamine, penicillamine methyl ester, penicilamine ethyl ester and/or the hydrochlorides of these compounds.

Prior to eluting the solution $L_2$, the cation exchanger is preferably washed with a wash solution, preferably water.

In the hydrolysis of a thiazolidine derivative according to the invention by means of an acidic cation exchanger in the $H^+$ form, the 2-aminomercaptan derivative which is formed binds (in the protonated form) to the cation exchanger. It is thus removed from the equilibrium. The carbonyl compound which is also formed and which is not present in cationic form does not bind to the cation exchanger and can easily be removed.

All acidic cation exchangers are suitable for the process according to the invention. Acidic cation exchangers are known and commercially available. A selection of different materials is compiled in Ullmann's Encyclopedia of Industrial Chemistry, Vol. A14, p. 451. As active ion-exchanging groups they contain, for example but not by limitation, carboxylic acid groups (weakly acidic cation exchangers), or sulfonic acid or phosphonic acid groups (strongly acidic cation exchangers). These acidic groups are capable of immobilizing the protonated aminomercaptan derivative.

In the process according to the invention, preference is given to using strongly acidic cation exchangers. Particular preference is given to using strongly acidic cation exchangers having sulfonic acid groups or phosphonic acid groups.

The reaction temperature in the process according to the invention can be varied within a wide range of preferably from +5 to +120° C., depending on the hydrolytic stability of the thiazolidine derivative used. Thiazolidine derivatives which are susceptible to hydrolysis, such as 2,2-dialkylthiazolidine derivatives, are preferably reacted at from +5 to +60° C., more preferably at from +5 to +40° C., whereas thiazolidine derivatives which are stable to hydrolysis, such as 2-monoalkylthiazolidine derivatives, or thiazolidine derivatives substituted by electron-withdrawing groups at the 2-position, are preferably reacted at from +15 to ±120° C., more preferably at from +40 to +100° C. The upper temperature limit depends essentially on the permanent temperature stability of the ion-exchange resins used, which is usually stated as being at most 120° C.

The pressure can likewise be varied within a wide range. It is preferably in a range between 0.05 and 4 bar, more preferably from 0.5 to 3 bar, and most preferably at from 0.8 to 1.2 bar. The reaction is particularly preferably carried out under atmospheric pressure.

The amount of cation exchanger used per mole of thiazolidine derivative depends on the capacity of the cation exchanger for the aminomercaptan derivative. In general, it corresponds approximately to the total capacity of the cation exchanger. Depending on the reaction temperature and the time the thiazolidine derivative solution is in contact with the exchange resin, preferably from 1 to 10 mol, more preferably from 1 to 3 mol, and most preferably from 1.05 to 2 mol of exchanger capacity are employed per mole of thiazolidine derivative.

The contact time of the thiazolidine derivative solution with the ion-exchanger resin also depends on the stability of the thiazolidine derivative hydrolyzed, and on the other parameters (temperature, pressure, amount of ion exchanger, concentration of the thiazolidine derivative) and is preferably between 10 s and 120 min, more preferably between 1 and 60 min, and most preferably between 1 and 40 min. The concentration of the thiazolidine derivative depends on its solubility in water and is preferably from 1 to 500 g/l, more preferably from 10 to 300 g/l, and most preferably from 30 to 200 g/l.

In a preferred embodiment of the process, the thiazolidine derivative flows through the cation exchanger, in a column, and eluted fractions are collected. The cation exchanger is subsequently washed out with water and eluted again with a suitable eluent. The thiazolidine derivative solution can be charged in an ascending or descending manner. It is preferably charged in an ascending manner.

The elution can be carried out in a cocurrent or countercurrent manner. It is preferably carried out in a countercurrent manner. Suitable eluents are aqueous solutions of inorganic bases, such as, for example, aqueous potassium hydroxide solution, aqueous sodium hydroxide solution, sodium carbonate, sodium bicarbonate or ammonia. It is also possible to use solutions of alkali metal salts, such as, for example, sodium chloride, potassium chloride or sodium sulfate.

In this two-step process, the cation exchanger is reconverted into the $H^+$ form after elution, by regenerating with an aqueous solution of an inorganic acid, such as, for example, hydrochloric acid or sulfuric acid.

However, the process is preferably carried out in one step, i.e. the aminomercaptan derivative is eluted directly using an acid, preferably an inorganic acid, such as, for example, hydrochloric acid or sulfuric acid, eluted fractions being collected, and the aminomercaptan derivative being obtained in the form of, for example, its hydrochloride or hydrogen sulfate. To obtain the free 2-aminomercaptan derivative, the acidic solution of the product can subsequently be neutralized by addition of base or by treatment with a basic anion exchanger. The 2-aminomercaptan derivative or its hydrochloride or hydrogen sulfate is isolated using customary methods, such as, for example, crystallization, extraction or distillation.

Using the one-step process, the cation exchanger is, after elution, once more present in the $H^+$ form and ready for the next reaction.

The process according to the invention is therefore also suitable for preparing 2-aminomercaptan derivatives and for preparing the corresponding carbonyl compounds from thiazolidine derivatives.

In particular, the process according to the invention is also suitable for obtaining cysteine, cysteine methyl ester or cysteine ethyl ester in optically active or racemic form from a thiazolidine derivative of the formula 2:

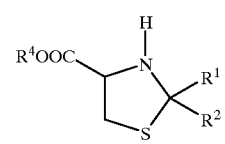

in which $R^1$ and $R^2$ are as defined under formula 1 and $R^4$ is H, methyl or ethyl.

Furthermore, the process according to the invention is suitable in particular for obtaining penicillamine, penicillamine methyl ester, or penicillamine ethyl ester in optically active or racemic form from a thiazolidine derivative of the formula 3:

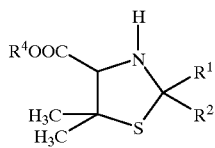

in which $R^1$ and $R^2$ are as defined under formula 1 and $R^4$ has the meaning H, methyl or ethyl.

The examples below serve to illustrate the invention in more detail.

EXAMPLE 1

Hydrolysis of (2Ξ,4R)-2-methylthiazolidine-2,4-dicarboxylic acid (CP)

Under an atmosphere of protective gas, a solution of 52.28 g of CP in 829 g of $H_2O$ was, at 90° C., introduced in an ascending manner into a column which contained 225 ml of a strongly acidic cation exchanger in the $H^+$ form (Rohm & Haas Amberjet® 1200). The ratio of height:diameter of the column was 4.48. The linear flow rate was 1.5 cm/min.

After all of the CP had been introduced, an amount of water was passed through the column in a cocurrent such that a total of 2.0 kg of a cleavage solution $L_1$ was obtained. Subsequently, likewise in a cocurrent manner, the column was eluted again with 2 N HCl and the eluted eluate solution $L_2$ (1.0 l) was collected.

According to HPLC, the solution $L_1$ contained 23.99 g of pyruvic acid (99.6%) and neither CP nor L-cysteine. According to HPLC, the solution $L_2$ contained 33.45 g (quant.) of L-cysteine and neither pyruvic acid nor CP.

EXAMPLE 2

Hydrolysis of (2RS,4RS)-2-isopropyl-5,5-dimethylthiazolidine-4-carboxylic acid (PI)

Under an atmosphere of protective gas, a solution of 55.58 g of PI in 1056 g of $H_2O$ was, at 90° C., introduced in an ascending manner into a column which contained 225 ml of a strongly acidic cation exchanger in the $H^+$ form (Rohm & Haas Amberjet® 1200). The ratio of height:diameter of the column was 4.48. The linear flow rate was 1.0 cm/min.

After all of the material had been introduced, an amount of water was passed through the column in a cocurrent such that a total of 2.0 kg of a cleavage solution $L_1$ were obtained. Likewise in a cocurrent manner, the column was then eluted with 2 N HCl, and the eluted eluate solution $L_2$ (1.01 l) was collected. According to GC, the solution $L_1$ contained 19.1 g of isobutyraldehyde (96.9%). According to HPLC, the solution $L_2$ contained 40.3 g (98.8 %) of DL-penicillamine and neither isobutyraldehyde nor PI.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the hydrolytic ring cleavage of thiazolidine derivatives to give 2-aminomercaptan derivatives and carbonyl compounds, comprising:
   a) contacting an aqueous solution of a thiazolidine derivative with an acidic cation exchanger in the $H^+$ form, giving a cleavage solution $L_1$ containing the carbonyl compound and
   b) eluting the cation exchanger with a suitable eluent, to provide a solution $L_2$ which contains the 2-aminomercaptan derivative wherein the thiazolidine derivatives used are compounds of the formula 1:

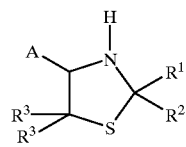

where

A is CN, $COOR^4$ or $CONR_5R_6$;

$R^4$ is CN, or a linear or branched $C_1$- to $C_{12}$-alkyl radical;

$R^5$ and $R^6$ are identical or different and are H or a linear or branched $C_1$- to $C_{12}$-alkyl radical;

$R^1$ and $R^2$ are identical or different and are H, a linear or branched $C_1$- to $C_{12}$-alkyl radical, a $C_1$- to $C_6$-alkyl radical which is mono- or polysubstituted by alkoxy or hydroxyl, $(CH_2)_nCOOR^4$ where n is an integer from 0 to 12 and $R^4$ is as defined above, a phenyl radical, or a phenyl, 1-naphthyl, 2-naphthyl, 9-phenanthrenyl, or 5- or 6-membered heteroaryl radical mono- or polysubstituted by $C_1$- to $C_6$-alkyl, said heteroaryl radical having 1 to 3 identical or different heteroatoms from the group consisting of O, N and S, or the radicals $R^1$ and $R^2$ together comprise a $C_2$- to $C_9$-cycloalkyl radical; and $R^3$ is H or methyl.

2. The process of claim 1, wherein the acidic cation exchanger used is a strongly acidic cation exchanger containing sulfonic acid groups or phosphonic acid groups.

3. The process of claim 1, wherein the reaction is carried out at a pressure between 0.05 and 4 bar.

4. The process of claim 1, wherein the ratio of cation exchanger to thiazolidine derivative is chosen such that from 1 to 10 mol of exchanger capacity are present per mole of thiazolidine derivative.

5. A process for obtaining a cysteine compound selected from the group consisting of cysteine, cysteine methyl ester and cysteine ethyl ester and mixtures thereof in optically active or racemic form from at least one thiazolidine derivative of the formula:

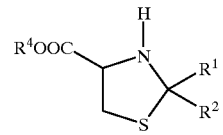

in which $R^1$ and $R^2$ are as defined under formula 1 and $R^4$ is H, methyl or ethyl, said process comprising:
   a) contacting an aqueous solution of the thiazolidine derivative of the formula 1 with an acidic cation exchanger in $H^+$ form, giving a cleavage solution $L_1$ which contains a carbonyl compound and
   b) eluting the cation exchanger with eluent to provide a solution $L_2$ which contains the cysteine compound.

6. A process for obtaining a compound selected from the group consisting of penicillamine, penicillamine methyl ester and penicillamine ethyl ester and mixtures thereof in optically active or racemic form from at least one thiazolidine derivative of the formula 3:

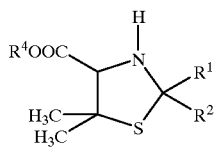

in which $R^1$ and $R^2$ are as defined under formula 1 and $R^4$ has the meaning H, methyl or ethyl, which comprises a) contacting an aqueous solution of the thiazolidine derivative with an acidic cation exchanger in H⁺ form, giving a cleavage solution $L_1$ which contains a carbonyl compound and b) eluting the cation exchanger with an eluent to provide a solution $L_2$ which contains the penicillamine compound.

7. The process of claim 2, wherein the ratio of cation exchanger to thiazolidine derivative is chosen such that from 1 to 10 mol of exchanger capacity are present per mole of thiazolidine derivative.

8. The process of claim 1, wherein the thiazolidine solution has a contact time with the cation exchanger of between 10 s and 120 min.

9. The process of claim 1, wherein the eluent is an aqueous solution of an alkali metal salt, an inorganic acid, or a base.

10. The process as claimed in claim 9, wherein the eluent is aqueous hydrochloric acid or sulfuric acid.

* * * * *